(12) United States Patent
Lippold et al.

(10) Patent No.: US 8,021,688 B2
(45) Date of Patent: Sep. 20, 2011

(54) FORMULATIONS OF ACTIVE COMPONENTS IN THE FORM OF A SOLID DISPERSION

(75) Inventors: Bernhard C. Lippold, Düsseldorf (DE); Nora Anne Urbanetz, Düsseldorf (DE)

(73) Assignee: Knoll GmbH, Ludwigshafen (DE)

( * ) Notice: Subject to any disclaimer, the term of this patent is extended or adjusted under 35 U.S.C. 154(b) by 1009 days.

(21) Appl. No.: 10/169,665

(22) PCT Filed: Jan. 10, 2001

(86) PCT No.: PCT/EP01/00224
§ 371 (c)(1),
(2), (4) Date: Oct. 29, 2002

(87) PCT Pub. No.: WO01/51025
PCT Pub. Date: Jul. 19, 2001

(65) Prior Publication Data
US 2003/0109639 A1 Jun. 12, 2003

(30) Foreign Application Priority Data
Jan. 11, 2000 (DE) .................... 100 00 792

(51) Int. Cl.
*A61K 9/14* (2006.01)
*A61K 9/48* (2006.01)
*A61K 47/32* (2006.01)
*C08L 39/04* (2006.01)

(52) U.S. Cl. ............ 424/489; 514/772.4; 525/205; 424/451

(58) Field of Classification Search .......... 514/772.4, 514/321; 424/489, 435, 451; 525/205
See application file for complete search history.

(56) References Cited

U.S. PATENT DOCUMENTS

| 4,289,749 | A | | 9/1981 | Keith |
| 4,292,104 | A | * | 9/1981 | Heimbach et al. ............ 156/235 |
| 4,321,263 | A | | 3/1982 | Powell |
| 4,764,378 | A | * | 8/1988 | Keith et al. .................. 424/435 |
| 5,164,277 | A | * | 11/1992 | Hirai et al. .................... 430/138 |
| 5,288,381 | A | * | 2/1994 | Cogan et al. ............ 204/192.26 |
| 5,294,615 | A | | 3/1994 | Meyer |
| 5,368,864 | A | * | 11/1994 | Lahr et al. .................... 424/489 |

(Continued)

FOREIGN PATENT DOCUMENTS
EP 232 877 8/1987
(Continued)

OTHER PUBLICATIONS

Sheth et al., "Biodegradable polymer blends of poly(lactic acid) and poly(ethylene glycol)" in Journal of Applied Polymer Science, pp. 1495-1505.*

(Continued)

*Primary Examiner* — Blessing Fubara
(74) *Attorney, Agent, or Firm* — Novak Druce + Quigg LLP

(57) ABSTRACT

Formulations of active compounds in the form of a solid dispersion, where the solid dispersion is formed from at least one active component and a carrier characterized in that the carrier is a mixture of polyvinylpyrrolidone (PVP) with a weight average molecular weight of $\leq 1\ 500\ 000$ Da and of a polyethylene glycol (PEG) which is semi-solid or solid at temperatures of 17 to 22° C. and has an average molar mass of 950 to 3300 Da.

28 Claims, 6 Drawing Sheets

U.S. PATENT DOCUMENTS

| | | | | |
|---|---|---|---|---|
| 5,599,583 | A | * | 2/1997 | Lew et al. ............. 427/213.3 |
| 5,637,319 | A | * | 6/1997 | Takada .................... 424/463 |
| 5,955,475 | A | * | 9/1999 | Krape et al. ............. 514/321 |
| 6,086,915 | A | * | 7/2000 | Zeligs et al. ............. 424/455 |
| 6,168,805 | B1 | | 1/2001 | Hein, II et al. |
| 6,238,284 | B1 | * | 5/2001 | Dittgen et al. ........... 424/443 |
| 6,391,338 | B1 | * | 5/2002 | Frisbee et al. ........... 424/487 |

FOREIGN PATENT DOCUMENTS

| | | |
|---|---|---|
| WO | 90/06115 | 6/1990 |
| WO | 93/11749 | 6/1993 |
| WO | 96/22103 | 7/1996 |

OTHER PUBLICATIONS

MOnzellBOchi/Schulz, Galenisches Praktikum, Wissenschaftliche Verlagsgesellschaft Stuttgart, 1959, p. 621.*

Fernandez et al. ("Dissolution kinetics of piroxicam in solid dispersions with polyethylene glycol 4000," in International journal of Pharmaceutics 98 (1993) abstract of pp. 29-35).*

Tantishaiyakul et al. ("properties of solid dispersions of piroxicam in polyvinylpyrrolidone K-30," in International Journal of Pharmaceutics 143 (1996) 59-660).*

Leuner et al. ("Improving drug solubility for oral delivery using solid dispersions," in European Journal of Pharmaceutics and Biopharmaceutics 50 (2000) 47-50.*

Genc et al. ("Studies on controlled release dimenhydrinate from matrix tablet formulations," in Pharmaceutica Acta Helvetiae 74 (1999) 43-49).*

Pharm.Ind.49, N4. 5(1987) Bioavailability and Erosive Activity of Solid Dispersion of . . . , Ramadan et al.

Fiedler, Lexikon der Hilfsstoffe, 3rd Ed. vol. 1, Cantor, Aulendorf 1989, p. 695, entry "Kollidon."

Hunnius, Pharmazeutisches Wörterbuch, de Gruyter, Berlin 1998, entry "Polyethylenglykole."

Münzel/Büchi/Schulz, Galenisches Praktikum, Wissenschaftliche Verlagsgesellschaft Stuttgart, 1959, p. 621.

Notice of Opposition pursuant to Article 99(1) EPC against European Patent No. 1 246 611, dated Jun. 18, 2008, pp. 1-15.

* cited by examiner

FORMULATIONS OF ACTIVE COMPONENTS IN THE FORM OF A SOLID DISPERSION

The present invention relates to formulations of active components as solid dispersion, the solid dispersion being formed from at least one active component and a carrier, to a carrier composed of polyvinylpyrrolidone (PVP) and polyethylene glycol (PEG), to a solvent-free process for producing the formulations of the invention, and to the use of molten PEG for dissolving PVP.

The poor solubility in water of many novel active components is increasingly giving rise to bioavailability problems. This is because poor solubility in water usually means that the active component likewise has poor solubility in the aqueous gastrointestinal fluid. However, since dissolving of the active component is the prerequisite for its absorption into the bloodstream, active components with poor solubility in water and, associated therewith, a low rate of dissolution prove to be critical.

The aim of pharmaceutical formulations in these cases must be to improve the dissolution properties in the gastrointestinal fluid. The rate of dissolution of the active component is, according to the law of Noyes and Whitney, proportional to the wetted area of the active component and the solubility of the active component in the gastrointestinal tract.

Both parameters can be influenced favorably by embedding the active component in an inert carrier which is readily soluble in water. The products are called solid dispersions. The degree of dispersibility of the active component in the dispersion determines its particle size and thus its surface area, and the degree of crystallinity determines its solubility in aqueous media. In addition, the hydrophilic carrier may improve the wetting.

In the prior art, solid dispersions are obtained by spray embedding, melt extrusion or melt embedding. Combined processes are also used.

Spray embeddings are produced by dissolving the active component, which is usually crystalline, with the carrier in a joint organic solvent. At this stage of production, both the medicinal substance and the carrier are no longer in the form of a molecular assemblage but are in the form of a molecular dispersion in the solution. Spraying the solution in a spray tower and evaporating the solvent result in a coprecipitate of active component and carrier, it being possible, depending on the properties of the two components, for the active component to remain as molecular dispersion in the carrier or else precipitate in amorphous or again in crystalline form. A typical carrier for spray embeddings is polyvinylpyrrolidone.

The disadvantages of the prior art process are, in particular, the very elaborate apparatus for spraying the solution and the subsequent recovery of solvent, which must be complete for reasons of environmental protection, but also for reasons of toxicity and storage stability of the final product. The advantage of the process is that, because of the recrystallization-inhibiting properties of polyvinylpyrrolidone, the active component preferentially results in the form of a molecular dispersion or in amorphous form in the carrier and remains in this form during storage too. This ensures an increased solubility and thus rate of dissolution of the active component in aqueous media, compared with active components which result as crystals.

The problems associated with solvents are avoided by producing melt extrudates by plasticizing the carrier with the active component and then shaping the plastic composition. A typical carrier for melt extrudates is polyvinylpyrrolidone.

If this process is to result in the active component in the form of a molecular dispersion or in amorphous form in the carrier, the crystalline active component must firstly during the production be converted into the state of a molecular dispersion. This is possible only if the active component is able to dissolve in the carrier. This often requires a not inconsiderable input of heat, leading, where appropriate, to the achievement of melting of at least one of the components. Active components which dissolve only if all the components have melted are no longer extrudable because the material is then liquid and has lost its plastic properties. In all other cases in which the active component cannot be converted into the state of a molecular dispersion during production, its original crystallinity is retained and the solubility in aqueous media is worse than that of final products containing amorphous active component. The apparatus for producing melt extrudates is very complicated.

Melt embeddings are obtained by melting the carrier material and dissolving the active component in the melt and subsequently cooling this solution. A typical carrier is polyethylene glycol.

The process has the least complicated apparatus compared with the two methods mentioned above. Production ensures, in contrast to melt extrusion, initially conversion of the active component into the state of a molecular dispersion, which is the prerequisite for the active component being in the form of a molecular dispersion or in the amorphous state in the final product. Moreover the thermal stress is usually low because of the low melting point of polyethylene glycol—between 35° C. and 60° C. depending on the molecular weight—and its good dissolving capacity in the molten state for many active components. However, the poorer recrystallization-inhibiting properties of polyethylene glycol compared with polyvinylpyrrolidone and its great tendency to crystallize itself mean that the active component may readily recrystallize during storage.

WO-A-90/06115 is cited as representative of a typical prior art mode of formulation of active components in the form of a solid dispersion. WO-A-90/06115 relates to preparations of oxipurinol and/or its alkali metal or alkaline earth metal salts in noncrystalline form comprising the active component in the form of a solid dispersion with pharmacologically acceptable excipients. They have a faster rate of dissolution and greater solubility than oxipurinol and/or its alkali metal or alkaline earth metal salts. They can be used to produce medicaments with high bioavailability of the active component oxipurinol. These preparations may also contain other active components or be mixed with the latter. The described preparations are produced for example by oxipurinol and/or its alkali metal or alkaline earth metal salts being dissolved together with the excipients or being dissolved in a melt of excipients, and the resulting melts or solutions being cooled and/or dried. Water is preferably used as solvent.

Suitable excipients are those which can either be melted or be dissolved with the aid of a solvent. Rapid cooling and/or drying of such melts or solutions results in solid dispersions or so-called "solid solutions" in which the oxipurinol is present in noncrystalline form.

The preparations described therein are produced, for example, by melting the active component and the excipients together and cooling by casting to give plates, dripping onto cooled substrates to give beads, pouring into preformed blisters or spray solidification. These melts can, where appropriate, also be metered directly into capsules.

The solutions can be produced, for example, by initially dissolving only the active component in the solvent and then admixing a solution of the excipients. It is also possible subsequently to introduce the active component into a solution of the aid. The removal of the solvent then takes place by vaporization, evaporation in vacuo, by spray-drying or freeze-drying.

Excipients employed for producing the oxipurinol solid dispersions are polyethylene glycols with average molecular weights of from 200 to about 35 000, polyvinylpyrrolidone (e.g. Kollidon® 17, 25, 30, 90), polyvinyl acetate, copolymers of polyvinylpyrrolidone/polyvinyl, acetate (e.g. Kollidon® VA 64), polyvinyl alcohols with very different degrees of hydrolysis, cellulose derivatives such as sodium carboxymethylcellulose, hydroxyethylcellulose, hydroxypropylmethylcellulose, acrylic acid derivatives such as polyacrylic acid (e.g. Carbopol®) alone or as mixture. Particularly preferred excipients are polyethylene glycols and polyvinylpyrrolidones.

The technical problem on which the invention was based was to provide a cost-effective process which is as simple as possible and does not use complicated apparatus but which avoids the problems associated with solvents with, at the same time, low thermal stress on the material and makes it possible to produce active component formulations in the form of a solid dispersion. The formulations were intended to have favorable active component release properties and retain them during storage. It was likewise intended that recrystallization of active components be suppressed.

The technical problem is solved by formulations of active components as solid dispersion, where the solid dispersion is formed from at least one active component and one carrier, characterized in that the carrier is a mixture of polyvinylpyrrolidone (PVP) with a weight average molecular weight of ≦1 500 000 Da and of a polyethylene glycol (PEG) which is semisolid or solid at temperatures of 17-22° C. and has an average molar mass of 950-3 300 Da.

The selection of PEG and PVP made according to the invention to achieve the formulations of the invention are not evident from WO-A-90/06115. It has been found, surprisingly, that polyvinylpyrrolidone dissolves in molten polyethylene glycol. This appears unusual because the miscibility of polymers with one another is energetically unfavorable because of the very small gain in entropy.

It has additionally been found that addition of polyvinylpyrrolidone is able to ensure the storage stability of melt embeddings based on polyethylene glycol with amorphous active component.

The currently commercially available products PEG 1000, PEG 1350, PEG 2000 and PEG 3000 are characterized by their average molar masses (polyethylene glycols, product description; Hoechst Aktiengesellschaft, Frankfurt am Main 1992.) The average molar mass of PEG 1000 is, for example, between 950 and 1 050 Da, that of PEG 3000 is between 2 700 and 3 300 Da. The corresponding molar mass distribution around the average molar mass follows from Poisson's formula (polyethylene glycols, product description; Hoechst Aktiengesellschaft, Frankfurt am Main 1992).

In the same way, the PVP commercial products are characterized with K values of 12, 17, 25, 30 and 90 via the weight average molecular weight (Bühler V.: Kollidon® Polyvinylpyrrolidone for the pharmaceutical industry; BASF Aktiengesellschaft Feinchemie, Ludwigshafen 1993). This is for PVP K12 for example 2 000 to 3 000 Da, and for PVP K90 1 000 000 to 1 500 000 Da. The corresponding molecular weight distribution around the weight average molecular weight corresponds in the ideal case to a Gaussian bell curve (Bühler V.: Kollidon® Polyvinylpyrrolidone for the pharmaceutical industry; BASF Aktiengesellschaft Feinchemie, Ludwigshafen 1993).

This broad specification, resulting from the production, concerning the molar mass of PEG and the molecular weight of PVP may in the extreme case influence the solubility of PVP in PEG or change the time taken to dissolve the PVP in PEG. In this connection, the solubility of PVP in PEG increases as the molecular weight of PVP decreases and the molar mass of PEG decreases.

The PEG:PVP ratio by weight in the formulations of the invention is preferably at least 0.25, with preference 0.25-19, in particular 1.5 to 9. In another preferred embodiment, the PEG:PVP ratio by weight is at least 1.0, preferably 1.0-19, in particular 1.5 to 9.

The weight average molecular weight of PVP is preferably ≦54 000 Da, in particular ≦34 000 Da or ≦11 000 Da.

The average molar mass of PEG in the formulations of the invention is preferably at values ≦2 200 Da.

Suitable as active component which can be used in the formulation of the invention is in principle any substance which interacts with the surroundings and brings about a change, which can be measured directly or indirectly, in the surroundings.

The active component is, in particular, a medicinal substance, prodrug, cosmetic agent, food supplement, crop protection agent, herbicide, pesticide, pest-control agent.

The invention also relates to a carrier composed of PVP with a weight average molecular weight of ≦1 500 000 Da and of a polyethylene glycol (PEG) which is semisolid or solid at temperatures of 17-22° C. and has an average molar mass of 950-3 300 Da. This carrier can be employed as intermediate in the production of a formulation of the invention, for example by melting the carrier of the invention and mixing with the active component.

The invention likewise relates to a solvent-free process for the production of the formulations of the invention. This entails PEG and PVP being mixed with active component and melted together in one process step, or PVP being dissolved in molten PEG, and then the active component being added, resulting in a molecular dispersion of the active component. After cooling, the active component formulation of the invention can then be obtained.

The active component formulations obtainable by the process of the invention surprisingly have a high storage stability.

A polyethylene glycol (PEG) which is semisolid or solid at temperatures of 17-22° C. and has an average molar mass of 950-3 300 Da is preferably used according to the invention for producing the solid dispersion. PVP is preferably employed with a weight average molecular weight of ≦1 500 000 Da.

The invention further relates to the use of a polyethylene glycol (PVG) which is semisolid or solid at temperatures of 17-22° C. and has an average molar mass of 950-3 300 Da in the molten state for dissolving PVP with a weight average molecular weight of ≦1 500 000 Da.

The invention is explained in more detail by means of the following examples.

EXAMPLES 1 AND 2

Production and Properties of Formulations

| Example 1: | | Example 2: | |
|---|---|---|---|
| Nimodipine | 20% | Nimodipine | 20% |
| PVP K 17 | 32% | PVP K 17 | 16% |
| PEG 2 000 | 48% | PEG 2 000 | 64% |

Solid dispersions of an active component with a mixture of polyethylene glycol 2 000 (average molar mass 1 800-2 200 Da) and polyvinylpyrrolidone K 17 (weight average molecular weight 7 000-11 000) are produced by melt embedding. For this purpose, firstly polyethylene glycol 2 000 was melted and then firstly polyvinylpyrrolidone K 17 and then nimodipine as active component were dissolved in the melt. The solution was poured into molds. Investigation of the release characteristics took place after one day and 4 and 24 weeks of storage.

Figure 1:
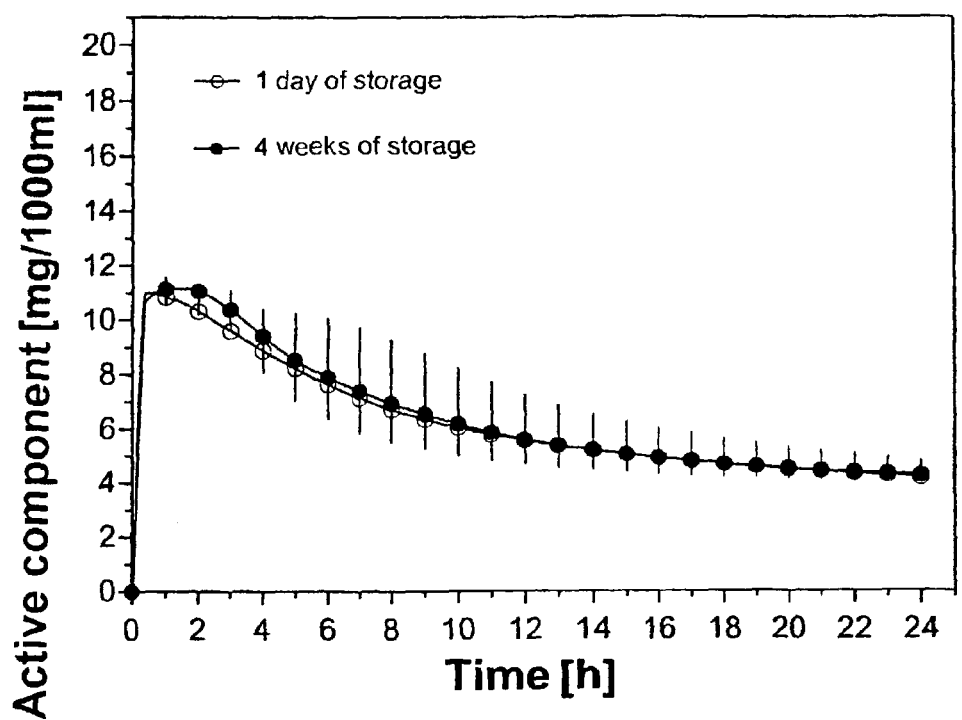
FIG. 1 shows the release profile from solid dispersions composed of 20% by weight nimodipine, 32% by weight polyvinylpyrrolidone K 17 and 48% by weight polyethylene glycol 2 000 (example 1) after one day and 4 weeks storage.

FIG. 1 shows the release profile from solid dispersions composed of 20% by weight nimodipine, 32% by weight polyvinylpyrrolidone K 17 and 48% by weight polyethylene glycol 2 000 (example 1) after one day and 4 weeks of storage. It is characterized by a high rate of release and a supersaturation of the active component in the release medium. These release characteristics are unchanged after 4 weeks of storage.

Figure 2:
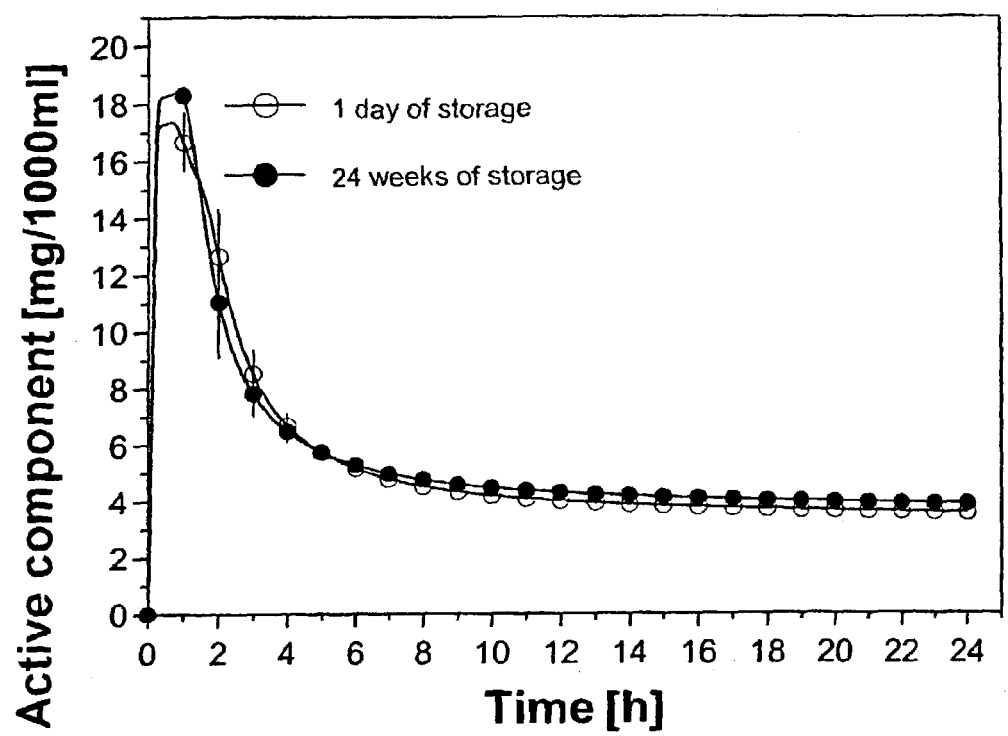
FIG. 2 shows the release profile from dispersions of 20% by weight % nimodipine, 16% by weight % polyvinylpyrrolidone K 17 and 64% by weight polyethylene glycol 2 000 (example 2) after one day and 24 weeks of storage.

FIG. 2 shows the release profile from dispersions of 20% by weight % nimodipine, 16% by weight % polyvinylpyrrolidone K 17 and 64% by weight polyethylene glycol 2 000 (example 2) after one day and 24 weeks of storage. It is characterized by a high rate of release and an extremely high supersaturation of the active component in the release medium. These release characteristics are unchanged after 24 weeks of storage.

Figure 3:
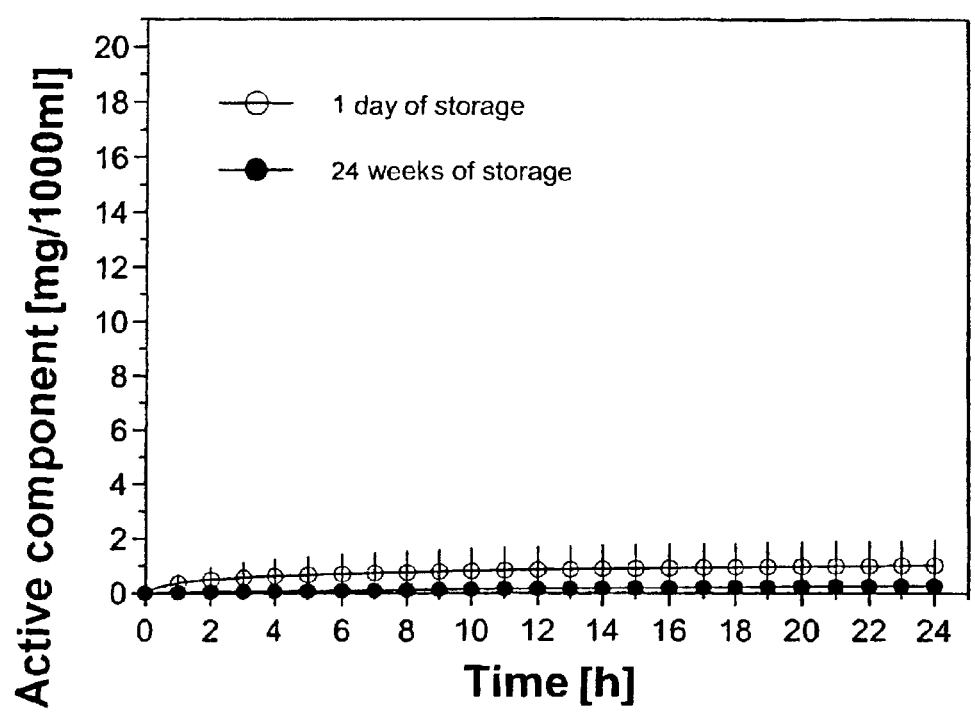
FIG. 3 demonstrates the release characteristics from solid dispersions without polyvinylpyrrolidone (80% by weight PEG 2 000 and 20% by weight nimodipine).

By contrast, FIG. 3 demonstrates the release characteristics from solid dispersions without polyvinylpyrrolidone (80% by weight PEG 2 000 and 20% by weight nimodipine). The rate of release is distinctly lower even after storage for one day compared with polyvinylpyrrolidone-containing products and deteriorates further after 24 weeks of storage.

Figure 4:
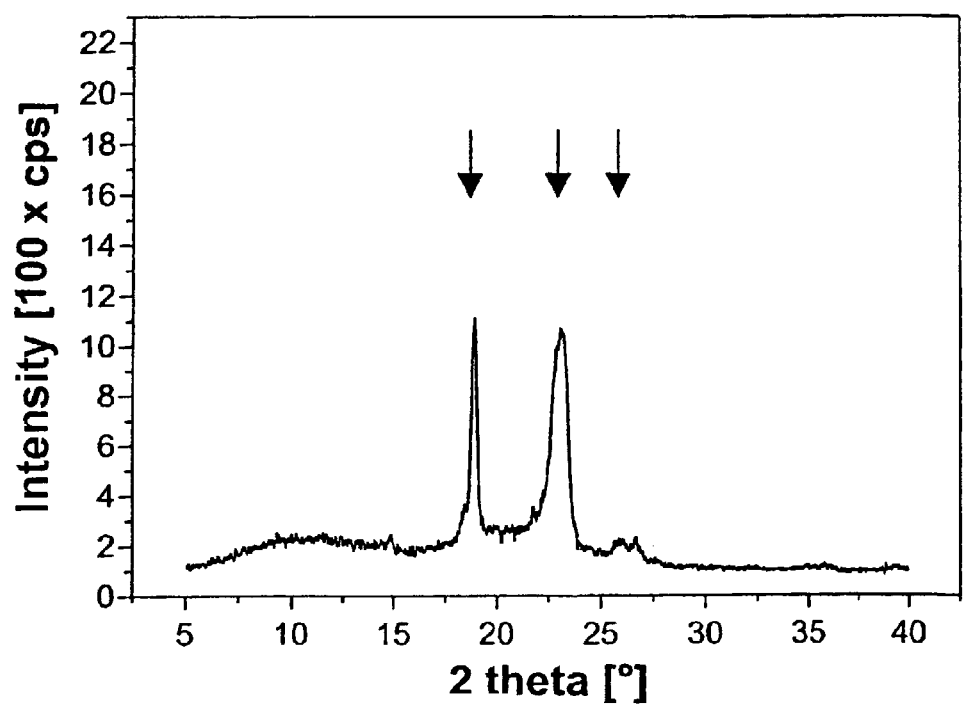
FIG. 4 shows the diffractogram of solid dispersions of 20% by weight nimodipine, 32% by weight polyvinylpyrrolidone K 17 and 48% by weight polyethylene glycol 2 000 (example 1) after 4 weeks of storage.
Figure 5:
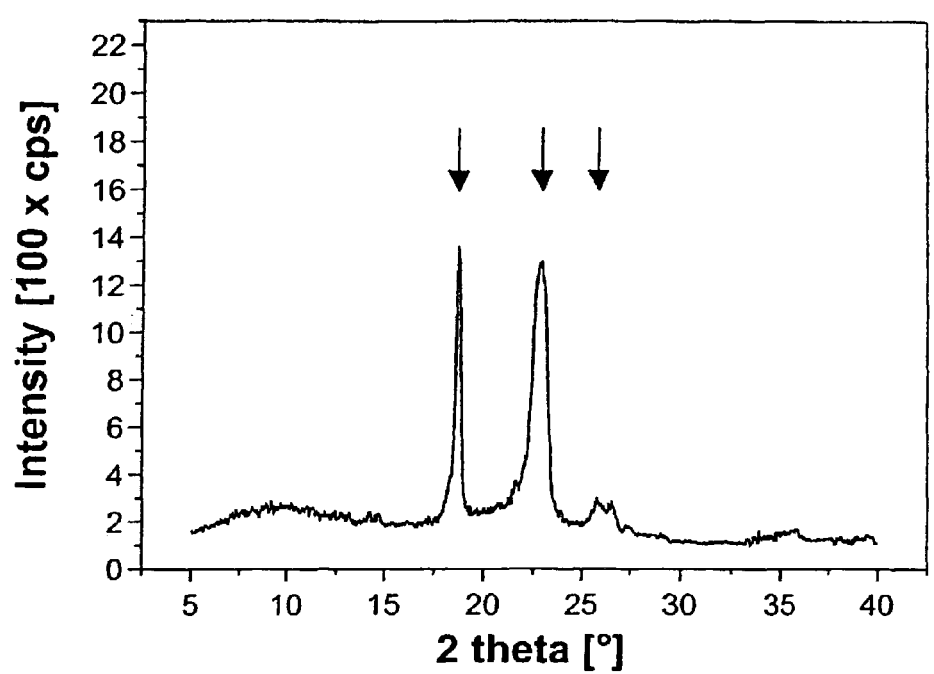
FIG. 5 shows the diffractogram of dispersions of 20% by weight % nimodipine, 16% by weight % polyvinylpyrrolidone K 17 and 64% by weight polyethylene glycol 2 000 (example 2) after 24 weeks of storage.

X-ray diffractometry investigations demonstrate that in the case of polyvinylpyrrolidone-free products the active component is in crystalline form after storage, whereas it remains in amorphous form in polyvinylpyrrolidone-containing products:

FIG. 4 shows the diffractogram of solid dispersions of 20% by weight nimodipine, 32% by weight polyvinylpyrrolidone K 17 and 48% by weight polyethylene glycol 2 000 (example 1) after 4 weeks of storage, and FIG. 5 shows the diffractogram of dispersions of 20% by weight % nimodipine, 16% by weight % polyvinylpyrrolidone K 17 and 64% by weight polyethylene glycol 2 000 (example 2) after 24 weeks of storage. The arrows in each case point to the signals of crystalline polyethylene glycol. There are no signs of crystalline active component.

Figure 6:
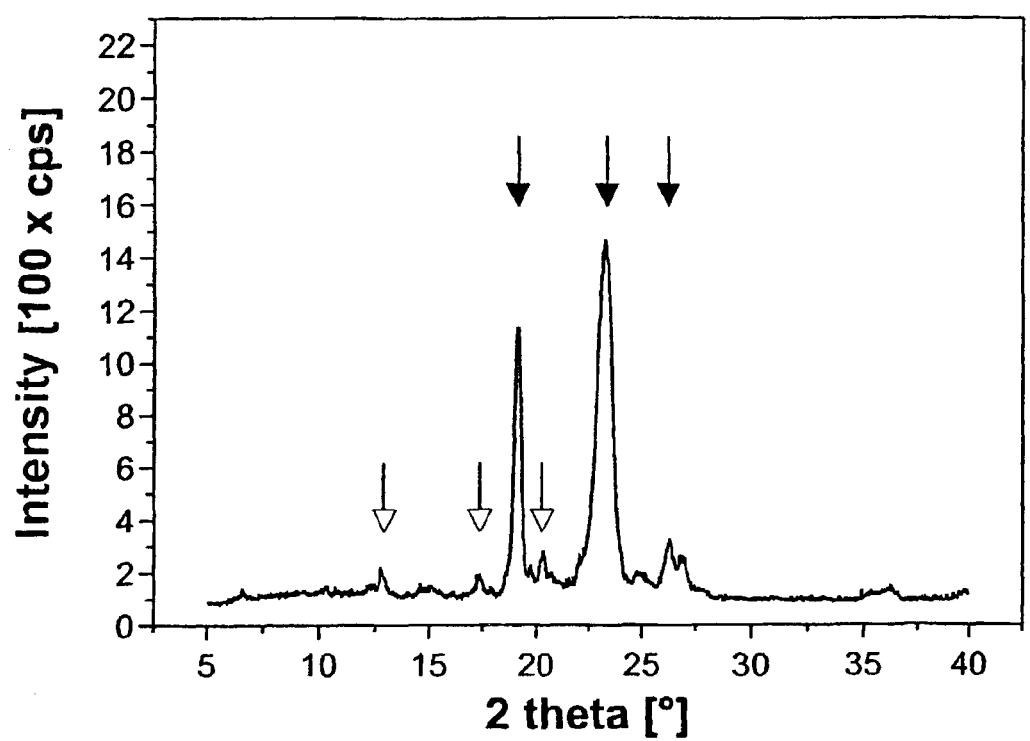
FIG. 6 shows the diffractogram of the polyvinylpyrrolidone-free products after 24 weeks of storage, the signals of crystalline polyethylene glycol are accompanied by signs of crystalline active component.

In contrast to this, in FIG. 6, which shows the diffractogram of the polyvinylpyrrolidone-free products after 24 weeks of storage, the signals of crystalline polyethylene glycol are accompanied by signs of crystalline active component. These are identified by arrows with open tips.

The results prove that addition of polyvinylpyrrolidone to solid dispersions based on polyethylene glycol is able to prevent recrystallization of the amorphous active component from the final product. Polyvinylpyrrolidone thus guarantees excellent storage stability of the polyethylene glycol melt embedding and constantly excellent release characteristics.

It has now become possible through the process of the invention to utilize the advantages of conventional melt embedding based on polyethylene glycol without needing to accept the disadvantage of storage instability.

Compared with known technologies, the process of the invention is distinguished by universal possibilities of use. Because the dissolving capacity of molten polyethylene glycol for many active components is good, the application is not confined to a few cases. The robust process allows formulations, in particular drug forms, with outstanding release properties and excellent storage stability to be produced with comparatively low technical complexity and avoiding the problems of organic solvents and high thermal stress.

EXAMPLES 3, 4, AND 5

Production of Carriers

EXAMPLE 3

PVP K12 80% (average molar mass 2 000-3 000 Da)
PEG1 000 20% (average molar mass 950-1 050 Da)

EXAMPLE 4

PVP K 90 60% (average molar mass 1 000 000-1 500 000 Da)
PEG1 000 40% (average molar mass 950-1 050 Da)

EXAMPLE 5

PVP K 12 5% (average molar mass 2 000-2 000 Da;
PEG 3 000 95% (average molar mass 2 700-3 300 Da)

The carriers composed of polyethylene glycol and polyvinylpyrrolidone were produced by melting the polyethylene glycol and then dissolving the polyvinylpyrrolidone. The solution was cooled and solidified to the solid carrier.

The invention claimed is:

1. A formulation of at least one active component as solid dispersion, wherein the solid dispersion is formed from at least one active component and one carrier, wherein the carrier consists of polyvinylpyrrolidone (PVP) with a weight average molecular weight of $\leqq 1,500,000$ Da and polyethylene glycol (PEG) which is semisolid or solid at temperatures of 17-22° C. and consists of one or more polyethyleneglycols, wherein each of the polyethyleneglycols has a single molar mass distribution which is distributed around an average molar mass, wherein the average molar mass is in each case in the range of from 950 to 3,300 Da, and wherein the at least one active component is in form of a molecular dispersion and is in amorphous form as determined by X-ray diffractometry.

2. The formulation of claim 1, characterized in that the PEG:PVP ratio by weight is at least 0.25.

3. The formulation of claim 1, characterized in that the PEG:PVP ratio by weight is at least 1.0.

4. The formulation of claim 1, characterized in that the weight average molecular weight of PVP is $\leq$54,000 Da.

5. The formulation of claim 1, the average molar mass is less than or equal to 2,200 Da.

6. The formulation of claim 1, characterized in that the active compound is a medicinal substance, cosmetic agent, food supplement, crop protection agent, herbicide, pesticide, pest-control agent.

7. The formulation of claim 1, wherein the average molar mass is 1000.

8. The formulation of claim 1, wherein the average molar mass is 1350.

9. The formulation of claim 1, wherein the average molar mass is 2000.

10. The formulation of claim 1, wherein the average molar mass is 3000.

11. A carrier composed of PVP with a weight average molecular weight of $\leq$1,500,000 Da and polyethylene glycol (PEG) which is semisolid or solid at temperatures of 17-22° C. and consists of one or more polyethyleneglycols, wherein each of the polyethyleneglycols has a single molar mass distribution which is distributed around an average molar mass, and wherein the average molar mass is in each case in the range of from 950 to 3,300 Da.

12. The formulation of claim 11, wherein the average molar mass is 1000.

13. The formulation of claim 11, wherein the average molar mass is 1350.

14. The formulation of claim 11, wherein the average molar mass is 2000.

15. The formulation of claim 11, wherein the average molar mass is 3000.

16. A process for producing a solid dispersion from at least one active component and a carrier, comprising mixing the at least one active component with the carrier, wherein the carrier is obtained by dissolving polyvinylpyrrolidone (PVP) in molten polyethylene glycol, wherein the polyvinylpyrrolidone has a weight average molecular weight of less than or equal to 1,500,000 Da and the polyethylene glycol (PEG) is semisolid or solid at temperatures of 17-22° C. and consists of one or more polyethylene glycols, wherein each of the polyethyleneglycols has a single molar mass distribution around an average molar mass which is in each case in a range of from 950 to 3,300 Da, wherein the polyethylene glycol to polyvinylpyrrolidone ratio by weight is from 0.25 to 19, to obtain the solid dispersion wherein the at least one active component is in form of a molecular dispersion and is in amorphous form as determined by X-ray diffractometry.

17. A process according to claim 16, wherein the process is carried out in the absence of solvent.

18. A process according to claim 16, wherein polyethylene glycol and polyvinylpyrrolidone are mixed with the active component and melted together in one process step.

19. A process according to claim 16, wherein the weight average molecular weight of PVP is less than or equal to 54,000 Da.

20. A process according to claim 16, wherein the PEG has a single molar mass distribution around an average molar mass of less than or equal to 2,200 Da.

21. A process according to claim 16, wherein the active component is a substance which interacts with the surroundings and brings about a change, which can be measured directly or indirectly, in the surroundings.

22. A process according to claim 16, wherein the active component is a medicinal substance, cosmetic agent, food supplement, crop protection agent, herbicide, pesticide, pest-control agent.

23. A process according to claim 16, wherein the PEG:PVP ratio by weight is from 0.25 to 19.

24. A process according to claim 16, wherein the PEG:PVP ratio by weight is from 1.0 to 19.

25. A process according to claim 16, wherein the PEG:PVP ratio by weight is from 1.5 to 9.

26. A process according to claim 16, wherein the weight average molecular weight of PVP is less than or equal to 34,000 Da.

27. A process according to claim 16, wherein the weight average molecular weight of PVP is $\leq$11,000 Da.

28. A formulation of active components comprising a solid dispersion obtained by the process of claim 16.

* * * * *